US012508427B2

(12) United States Patent
Durand et al.

(10) Patent No.: US 12,508,427 B2
(45) Date of Patent: Dec. 30, 2025

(54) CLOSED-LOOP VAGUS NERVE STIMULATION FOR THE TREATMENT OF OBESITY

(71) Applicant: Case Western Reserve University, Cleveland, OH (US)

(72) Inventors: Dominique Durand, Shaker Heights, OH (US); Joseph Marmerstein, Cleveland, OH (US); Grant McCallum, South Euclid, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 361 days.

(21) Appl. No.: 18/119,329

(22) Filed: Mar. 9, 2023

(65) Prior Publication Data

US 2023/0310863 A1 Oct. 5, 2023

Related U.S. Application Data

(60) Provisional application No. 63/317,997, filed on Mar. 9, 2022.

(51) Int. Cl.
*A61N 1/36* (2006.01)
*A61N 1/372* (2006.01)

(52) U.S. Cl.
CPC ..... *A61N 1/36139* (2013.01); *A61N 1/36053* (2013.01); *A61N 1/36085* (2013.01); *A61N 1/3727* (2013.01)

(58) Field of Classification Search
None
See application file for complete search history.

(56) References Cited

U.S. PATENT DOCUMENTS 5,263,480 A * 11/1993 Wernicke ........... A61N 1/36007 607/133
10,154,922 B1 * 12/2018 Perez .................. A61N 1/0502
(Continued)

OTHER PUBLICATIONS

Marmerstein, Joseph T., Grant A. McCallum, and Dominique M. Durand. "Direct measurement of vagal tone in rats does not show correlation to HRV." Scientific reports 11.1 (2021): 1-12.
(Continued)

*Primary Examiner* — Mallika D Fairchild
(74) *Attorney, Agent, or Firm* — Tarolli, Sundheim, Covell & Tummino LLP

(57) ABSTRACT

Obesity and other medical conditions can be managed using a closed-loop system, which uses one or more implantable recording electrodes, a processing device, and one or more implantable stimulating electrodes. The one or more implantable recording electrodes can record signals from a portion of one or more subdiaphragmatic branches of a patient's vagus nerve. The processing device can be configured to: receive the signals from the portion of the one or more subdiaphragmatic branches of the patient's vagus nerve, perform signal processing to decode the signals from the portion of the one or more subdiaphragmatic branches of the patient's vagus nerve, and configure a stimulation to decrease the patient's hunger and/or increase the patient's satiety based on the decoded signals. The one or more implantable stimulating electrodes can deliver the configured stimulation to another portion of one or more subdiaphragmatic branches of the patient's vagus nerve.

16 Claims, 14 Drawing Sheets

(56) References Cited

U.S. PATENT DOCUMENTS

| | | | | |
|---|---|---|---|---|
| 2002/0087192 A1* | 7/2002 | Barrett | A61N 1/36085 | 607/2 |
| 2005/0038484 A1* | 2/2005 | Knudson | A61N 1/36071 | 607/58 |
| 2005/0070974 A1* | 3/2005 | Knudson | A61N 1/36007 | 607/58 |
| 2015/0141786 A1* | 5/2015 | Durand | A61N 1/0558 | 607/116 |

OTHER PUBLICATIONS

Hill DN, Mehta SB, Kleinfeld D. Quality metrics to accompany spike sorting of extracellular signals. J Neurosci. Jun. 15, 2011;31(24):8699-705. doi: 10.1523/JNEUROSCI.0971-11.2011. PMID: 21677152; PMCID: PMC3123734.

Ciao, D., Cai, J., Brancati, F. L., Folsom, A., Barnes, R. W., Tyroler, H. A., & Heiss, G. (1995). Association of vagal tone with serum insulin, glucose, and diabetes mellitus—The ARIC Study. Diabetes Research and Clinical Practice, 30(3), 211-221. doi:10.1016/0168-8227(95)01190-0.

Ronkainen, E, Korpelainen JT, Heikkinen E, Myllyla VV, Huikuri HV, Isojarvi JI. Cardiac autonomic control in patients with refractory epilepsy before and during vagus nerve stimulation treatment: a one-year follow-up study. Epilepsia. Mar. 2006,47(3):556-62. doi: 10.1111/j.1528-1167.2006.00467.x. PMID: 16529621.

Sivakumar SS, Namath AG, Tuxhorn IE, Lewis SJ, Galan RF. Decreased heart rate and enhanced sinus arrhythmia during interictal sleep demonstrate autonomic imbalance in generalized epilepsy. J Neurophysiol. Apr. 2016;115 (4): 1988-99. doi: 10.1152/jn.01120.2015. Epub Feb. 17, 2016. PMID: 26888110; PMCID: PMC4869507.

Grassi, Guido. "Assessment of sympathetic cardiovascular drive in human hypertension: achievements and perspectives." Hypertension 54.4 (2009): 690-697.

Porges, Stephen W. "Cardiac vagal tone: a physiological index of stress." Neuroscience & Biobehavioral Reviews 19.2 (1995): 225-233.

Gidron, Y.; Deschepper, R.; De Couck, M.; Thayer, J.F.; Velkeniers, B. The Vagus Nerve Can Predict and Possibly Modulate Non-Communicable Chronic Diseases: Introducing a Neuroimmunological Paradigm to Public Health. J. Clin. Med. 2018, 7, 371. https://doi.org/10.3390/jcm7100371.

Fan, Jing-Jing, et al. "Research progress of vagus nerve stimulation in the treatment of epilepsy." CNS neuroscience & therapeutics 25.11 (2019): 1222-1228.

Cracchiolo, Marina, et al. "Bioelectronic medicine for the autonomic nervous system: clinical applications and perspectives." Journal of Neural Engineering 18.4 (2021): 041002.

Mei, N., M. Condamin, and A. Boyer. "The composition of the vagus nerve of the cat." Cell and tissue research 209 (1980): 423-431.

Prechtl, James C., and Terry L. Powley. "The fiber composition of the abdominal vagus of the rat." Anatomy and embryology 181 (1990): 101-115.

Kral, John G., et al. "Gastroplasty for obesity: long-term weight loss improved by vagotomy." World journal of surgery 17 (1993): 75-78.

Smith, D., Sarfeh, J., & Howard, L. (1983). Truncal Vagotomy in Hypothalamic Obesity. The Lancet, 321 (8337), 1330-1331. doi:10.1016/s0140-6736(83)92437-6.

Prologo, J. D., Lin, E., Horesh Bergquist, S., Knight, J., Matta, H., Brummer, M., . . . Corn, D. (2019). Percutaneous CT-Guided Cryovagotomy in Patients with Class I or Class II Obesity: A Pilot Trial. Obesity, 27(8), 1255-1265. doi:10.1002/oby.22523.

Loper H, Leinen M, Bassoff L, Sample J, Romero-Ortega M, Gustafson KJ, Taylor DM, Schiefer MA. Both high fat and high carbohydrate diets impair vagus nerve signaling of satiety. Sci Rep. May 17, 2021;11(1):10394. doi: 10.1038/s41598-021-89465-0. PMID: 34001925; PMCID: PMC8128917.

Kral, John G., Wencesley Paez, and Bruce M. Wolfe. "Vagal nerve function in obesity: therapeutic implications." World journal of surgery 33 (2009): 1995-2006.

Tan DW, Schiefer MA, Keith MW, Anderson JR, Tyler J, Tyler DJ. A neural interface provides long-term stable natural touch perception. Sci Transl Med. Oct. 8, 2014;6(257):257ra138. doi: 10.1126/scitranslmed.3008669. PMID: 25298320; PMCID: PMC5517305.

Dweiri, Y. M., Eggers, T. E., Gonzalez-Reyes, L. E., Drain, J., McCallum, G. A., & Durand, D. M. (2017). Stable Detection of Movement Intent From Peripheral Nerves: Chronic Study in Dogs. Proceedings of the IEEE, 105(1), 50-65. doi: 10.1109/jproc.2016.2607520.

Eggers, Thomas E., et al. "Recovering motor activation with chronic peripheral nerve computer interface." Scientific Reports 8.1 (2018): 14149.

Sabetian, P., Y. Sadat-Nejad, and Paul B. Yoo. "Classification of directionally specific vagus nerve activity using an pper airway obstruction model in anesthetized rodents." Scientific Reports 11.1 (2021): 1-13.

Koh, Ryan GL, Adrian I. Nachman, and Jose Zariffa. "Classification of naturally evoked compound action potentials in peripheral nerve spatiotemporal recordings." Scientific reports 9.1 (2019): 1-13.

Lago N, Yoshida K, Koch KP, Navarro X. Assessment of biocompatibility of chronically implanted polyimide and platinum intrafascicular electrodes. IEEE Trans Biomed Eng. Feb. 2007;54(2):281-90. doi: 10.1109/TBME.2006.886617. PMID: 17278585.

Badia J, Boretius T, Pascual-Font A, Udina E, Stieglitz T, Navarro X. Biocompatibility of chronically implanted transverse intrafascicular multichannel electrode (TIME) in the rat sciatic nerve. IEEE Trans Biomed Eng. Aug. 2011;58 (8). doi: 10.1109/TBME.2011.2153850. Epub May 12, 2011. PMID: 21571604.

Rijnbeek EH, Eleveld N, Olthuis W. Update on Peripheral Nerve Electrodes for Closed-Loop Neuroprosthetics. Front Neurosci. May 28, 2018;12:350. doi: 10.3389/fnins.2018.00350. PMID: 29910705; PMCID: PMC5992394.

Kiman, Ahmad A., et al. "Multi-channel intraneural vagus nerve recordings with a novel high-density carbon fiber microelectrode array." Scientific Reports 10.1 (2020): 1-13.

Patel, Paras R., et al. "High density carbon fiber arrays for chronic electrophysiology, fast scan cyclic voltammetry, and correlative anatomy." Journal of Neural Engineering 17.5 (2020): 056029.

McCallum, Grant A., et al. "Chronic interfacing with the autonomic nervous system using carbon nanotube (CNT) yarn electrodes." Scientific reports 7.1 (2017): 11723.

Ozaki, Noriyuki, J. N. Sengupta, and G. F. Gebhart. "Mechanosensitive properties of gastric vagal afferent fibers in the rat." Journal of neurophysiology 82.5 (1999): 2210-2220.

Schwartz, Gary J., Paul R. McHugh, and Timothy H. Moran. "Integration of vagal afferent responses to gastric loads and cholecystokinin in rats." American Journal of Physiology-Regulatory, Integrative and Comparative Physiology 261.1 (1991): R64-R69.

Date, Yukari, et al. "The role of the gastric afferent vagal nerve in ghrelin-induced feeding and growth hormone secretion in rats." Gastroenterology 123.4 (2002): 1120-1128.

Strader, April D., and Stephen C. Woods. "Special Reports and Reviews-Gastrointestinal hormones and food Intake." Gastroenterology-Orlando 128.1 (2005): 175-191.

Davison JS, Grundy D. Modulation of single vagal efferent fibre discharge by gastrointestinal afferents in the rat. J Physiol. Nov. 1978;284:69-82. doi: 10.1113/jphysiol.1978.sp012528. PMID: 731576; PMCID: PMC1282809.

Deisseroth, K.; Clarity Resource Center. Available online: http://clarityresourcecenter.org/ (accessed on Jun. 15, 2023).

Chung K, Deisseroth K. Clarity for mapping the nervous system. Nat Methods. Jun. 2013;10(6):508-13. doi: 10.1038/nmeth.2481. Erratum in: Nat Methods. Oct. 2013;10(10):1035. PMID: 23722210.

Zheng, Y. Design and Fabrication of a Highly Flexible Neural Interface. Ph.D. Dissertation, CaseWestern Reserve University, Cleveland, OH, USA, 2017.

(56) References Cited

OTHER PUBLICATIONS

Groves, Duncan A., and Verity J. Brown. "Vagal nerve stimulation: a review of its applications and potential mechanisms that mediate its clinical effects." Neuroscience & Biobehavioral Reviews 29.3 (2005): 493-500.
Pardo JV, Sheikh SA, Kuskowski MA, Surerus-Johnson C, Hagen MC, Lee JT, Rittberg BR, Adson DE. Weight loss during chronic, cervical vagus nerve stimulation in depressed patients with obesity: an observation. Int J Obes (Lond). Nov. 2007;31(11):1756-9. doi: 10.1038/sj.ijo.0803666. Epub Jun. 12, 2007. PMID: 17563762; PMCID: PMC2365729.
Johnson, Rhaya L., and Christopher G. Wilson. "A review of vagus nerve stimulation as a therapeutic intervention." Journal of inflammation research (2018): 203-213.
Murakami, N., et al. "Role for central ghrelin in food intake and secretion profile of stomach ghrelin in rats." Journal of Endocrinology 174.2 (2002): 283-288.
Schwartz, Gary J., et al. "Relationships between gastric motility and gastric vagal afferent responses to CCK and GRP in rats differ." American Journal of Physiology-Regulatory, Integrative and Comparative Physiology 272.6 (1997): R1726-R1733.
Schwartz, Gary J., Paul R. McHugh, and Timothy H. Moran. "Gastric loads and cholecystokinin synergistically stimulate rat gastric vagal afferents." American Journal of Physiology-Regulatory, Integrative and Comparative Physiology 265.4 (1993): R872-R876.
Marques, Cláudia, et al. "High-fat diet-induced obesity Rat model: a comparison between Wistar and Sprague-Dawley Rat." Adipocyte 5.1 (2016): 11-21.
Johannessen, Helene, et al. "Vagal blocking for obesity control: a possible mechanism-of-action." Obesity surgery 27 (2017): 177-185.
Sarr, Michael G., et al. "The EMPOWER study: randomized, prospective, double-blind, multicenter trial of vagal plockade to induce weight loss in morbid obesity." Obesity surgery 22 (2012): 1771-1782.
Horbach T, Thalheimer A, Seyfried F, Eschenbacher F, Schuhmann P, Meyer G. abiliti Closed-Loop Gastric Electrical Stimulation System for Treatment of Obesity: Clinical Results with a 27-Month Follow-Up. Obes Surg. Oct. 2015;25(10):1779-87. doi: 10.1007/s11695-015-1620-z. PMID: 25771794; PMCID: PMC4559577.
Horbach, T., et al. "Closed-loop gastric electrical stimulation versus laparoscopic adjustable gastric band for the treatment of obesity: a randomized 12-month multicenter study." International Journal of Obesity 40.12 (2016): 1891-1898.

* cited by examiner

CLOSED-LOOP VAGUS NERVE STIMULATION FOR THE TREATMENT OF OBESITY

CROSS-REFERENCE TO RELATED APPLICATIONS

This application claims the benefit of U.S. Provisional Application No. 63/317,997 filed Mar. 9, 2022, entitled, "CLOSED-LOOP VAGUS NERVE STIMULATION FOR THE TREATMENT OF OBESITY". This application is hereby incorporated by reference in its entirety for all purposes.

GOVERNMENT FUNDING

This invention was made with government support under W81XWH-18-1-0581 awarded by Congressionally Directed Medical Research Programs and 5R01 NS032845-22 awarded by National Institutes of Health. The government has certain rights in the invention.

TECHNICAL FIELD

The present disclosure relates to treating obesity (or other gastric/metabolic disorders), and, more specifically, to systems and methods for the treatment of obesity (or other gastric/metabolic disorders) via closed-loop vagus nerve stimulation (VNS).

BACKGROUND

Obesity, defined as a body mass index (BMI) over 30, is a global epidemic. As of 2016 13% of adults worldwide are considered obese, a number that has nearly tripled since 1975. Elevated BMI significantly increases risk of premature death and chronic diseases such as heart disease, stroke, diabetes, and come cancers. Obesity can be prevented or reduced by changes in diet and exercise habits; however, these behavioral changes are often not adequate for sustained weight loss. Gastric surgery can be effective in the long-term but can have deleterious effects because it is an invasive surgery. Given the increasing rates of adult and child obesity, new therapies are needed which can provide alternatives to major surgery.

The vagus nerve contains a variety of bidirectional signaling pathways between the brain and internal organs, but the majority of vagal fibers are gastric afferents, which are involved in the regulation of food intake via signaling of hunger and satiety (feeling full). Open-loop vagus nerve stimulation (VNS) has been used to induce weight loss in obese patients, though the mechanism by which these therapies cause weight loss is not well understood. In fact, most VNS studies have showed inconsistent results.

SUMMARY

Closed-loop vagus nerve stimulation (VNS) may be a key to improving consistency and effectiveness in the treatment of obesity (or other gastric/metabolic disorders).

In one aspect, the present disclosure includes a system for closed-loop VNS for the treatment of obesity (or other gastric/metabolic disorders). The system includes one or more implantable recording electrodes to record signals from a portion of one or more subdiaphragmatic branches of a patient's vagus nerve. The system also includes a processing device configured to: receive the signals from the portion of the one or more subdiaphragmatic branches of the patient's vagus nerve, perform signal processing to decode the signals from the portion of the one or more subdiaphragmatic branches of the patient's vagus nerve, and configure a stimulation to decrease the patient's hunger and/or increase the patient's satiety based on the decoded signals. The system also includes one or more implantable stimulating electrodes to deliver the configured stimulation to another portion of one or more subdiaphragmatic branches of the patient's vagus nerve.

In another aspect, the present disclosure includes a method for closed-loop VNS for the treatment of obesity (or other gastric/metabolic disorders). Steps of the method can be performed by a system that includes a processor. The steps include:

- receiving signals recorded by one or more implanted recording electrode positioned in a portion of one or more subdiaphragmatic branches of a patient's vagus nerve;
- performing signal processing to decode the signals from the portion of the one or more subdiaphragmatic branches of the patient's vagus nerve; and configuring a stimulation to decrease the patient's hunger and/or increase the patient's satiety based on the decoded signals when delivered to another portion of one or more subdiaphragmatic branches of the patient's vagus nerve by one or more implanted stimulating electrodes.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

As used herein, the singular forms "a," "an," and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "vagus nerve" can refer to the longest cranial nerve, passing through the neck and thorax to the abdomen. The vagus nerve contains efferent and afferent fibers from the autonomic nervous system related to various bodily organs.

As used herein, the term "subdiaphragmatic", when describing the vagus nerve, refers to branches of the vagus nerve located beneath the diaphragm and serves as a major modulatory pathway between the brain and the gut. In fact, one function the subdiaphragmatic vagus nerve is responsible for is regulating gastric functions, including digestion.

Figure 2:
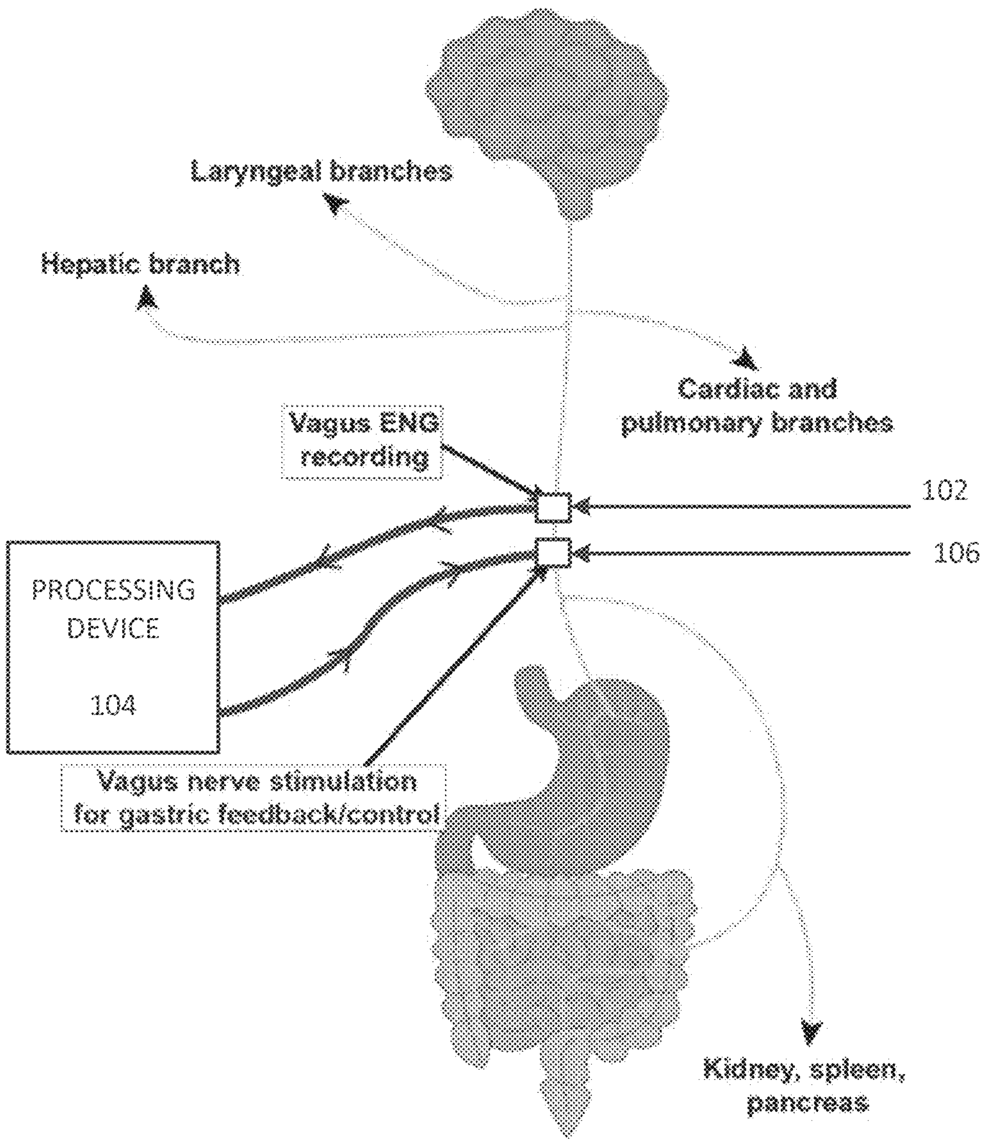
FIG. 2 is an illustration showing how elements of the system of FIG. 1 can be implanted.

As used herein the term "branches" refer to portions of the vagus nerve innervating various organs. An example of the different branches of the vagus nerve is shown in FIG. 2.

As used herein, the term "closed-loop" refers to a system that receives feedback and configures a stimulation based on the feedback.

As used herein, the term "patient" refers to a mammal (e.g., a human) suffering from obesity (or other gastric/metabolic disorders or conditions like irritable bowel disease, diabetes, hypertension, trouble eating, or the like).

II. Overview

The vagus nerve innervates nearly every internal organ, providing sensory input to the brain and parasympathetic-control inputs to the viscera. Therefore, abnormal vagus-nerve activity has been linked to many chronic diseases, such as epilepsy, diabetes, hypertension, and cancer. The majority of vagal afferent fibers come from the gut, and abnormal vagal activity has been clearly implicated in obesity and other gastric/metabolic disorders. Open-loop vagus nerve stimulation (VNS) has been used to induce weight loss in obese patients, though the mechanism by which these therapies cause weight loss is not well understood; however, most VNS studies have showed inconsistent results. Described herein are closed-loop VNS systems and methods for the treatment of obesity and other gastric/metabolic disorders. The closed-loop VNS systems can record vagal activity (in the form of electrical signals) related to gastric events from a subdiaphragmatic branch of the vagus nerve, decode the vagal activity related to these events (which can involve matching to a previously decoded signal), and deliver a stimulation to another subdiaphragmatic branch of the vagus nerve.

III. System

An aspect of the present disclosure can include a system 100 for closed-loop vagus nerve stimulation for obesity control (and/or treatment of other metabolic/gastric conditions). The system 100 includes one or more implantable recording electrodes 102 to record signals from a portion of one or more subdiaphragmatic branches of a patient's vagus nerve; a processing device 104 configured to: receive 108 the signals from the portion of the one or more subdiaphragmatic branches of the patient's vagus nerve, perform signal processing 110 to decode the signals from the portion of the one or more subdiaphragmatic branches of the patient's vagus nerve, and configure 112 a stimulation to decrease the patient's hunger and/or increase the patient's satiety based on the decoded signals; and one or more implantable stimulating electrodes 106 to deliver the configured stimulation to another portion of one or more subdiaphragmatic branches of the patient's vagus nerve. In other words, the recording electrode(s) 102 can recording of spontaneous vagal activity in order to detect eating-related signals and decode patient condition (by the processing device 104, for example the patient condition can be eating, not eating, should be full, should be hungry, full, hungry, or the like), and a stimulation can be configured based on the decoded patient condition and delivered by the stimulating electrode(s) 106. In some instances, the cycle can keep going after the stimulation is delivered when a new reading is acquired until a preset value is reached at the recording and the cycle stops. The system 100 can provide closed-loop vagus nerve stimulation to reduce stimulation time, power requirements, and adverse side effects.

The recording electrode(s) 102 and stimulating electrode(s) (stimulation electrode(s) 106) can be implanted proximal to or within the subdiaphragmatic branches of the vagus nerve. Such implantation can minimize off-target recordings and stimulation side-effects. The recording electrode(s) 102 and/or stimulating electrode(s) can be, for example, cuff electrodes, loose electrodes, or intrafascicular electrodes (at least a portion of which can be configured to be implanted intrafascicularly). As an example, at least a portion of intrafascicular electrodes can be made of a carbon nanotube yarn or other material that can be used in an intrafascicular electrode. The processing device 104 can be located outside the body of the patient (e.g., a computing device such as a mobile device or computer) and/or implanted within the body of the patient (e.g., as a signal processing chip) because the signal processing and stimulus control could be done via a fully implantable system, or with the aid of external processing. Because the regulation of food intake is a relatively slow process (changes occurring on the order of seconds or minutes), the processing device (comprising at least a processor, such as a hardware processor and a memory, such as a non-transitory memory) can be outside of the patient, such as on a mobile device or computer, in some instances. As another examples, each of the components can be implantable as separate pieces in communication with each other or even combined in a single implantable device.

For example, signals recorded from the nerve by the recording electrode(s) 102 are sent to the processing device 104, which analyzes (or decodes) data and also may save the data and/or the results of the analysis for further use. As another example, after implantation and surgery recovery the system 100 would require a training period, where the patient would indicate their times of hunger, amount, and length of food intake, and/or satiety feelings after meals. The training period can be used to match vagal activity with specific eating/satiation events. After the training period, recorded vagal signals would be decoded by the signal processing device 104, which would then control stimulation to produce the desired effect (e.g., reduction in hunger when a certain vagal activity is decoded and a certain stimulation is delivered) while lessening off-stream reactions and unrelated/undesired consequences by minimizing the amount of stimulation used.

In treating obesity, for example, the system 100 is intended to stimulate the vagus nerve to either decrease hunger or induce satiety in order to reduce food intake. FIG. 2 shows an example of where the elements of the system 100 can be located. Recording electrode(s) 102 can be used to record signals in the subdiaphragmatic vagus nerve branch(es), which are then decoded by the processing device 104 and the decoded signals can be used to drive vagal nerve stimulation delivered by the stimulating electrode(s) 104. For example, the decoded vagus nerve signals can be used to determine optimal timing and/or type of vagus nerve stimulation.

FIG. 2 illustrates the relative locations of several key vagus nerve branches, and the proposed target for both vagus nerve recording and stimulation. When detecting vagal signals of hunger, a blocking stimulus can be applied to reduce the patient's hunger. During and after eating, when feelings of satiety help the patient control the amount of food intake, stimulation of the vagus nerve could enhance these signals in order to reduce hunger and thereby decrease the patient's meal size.

IV. Method

Figure 1:
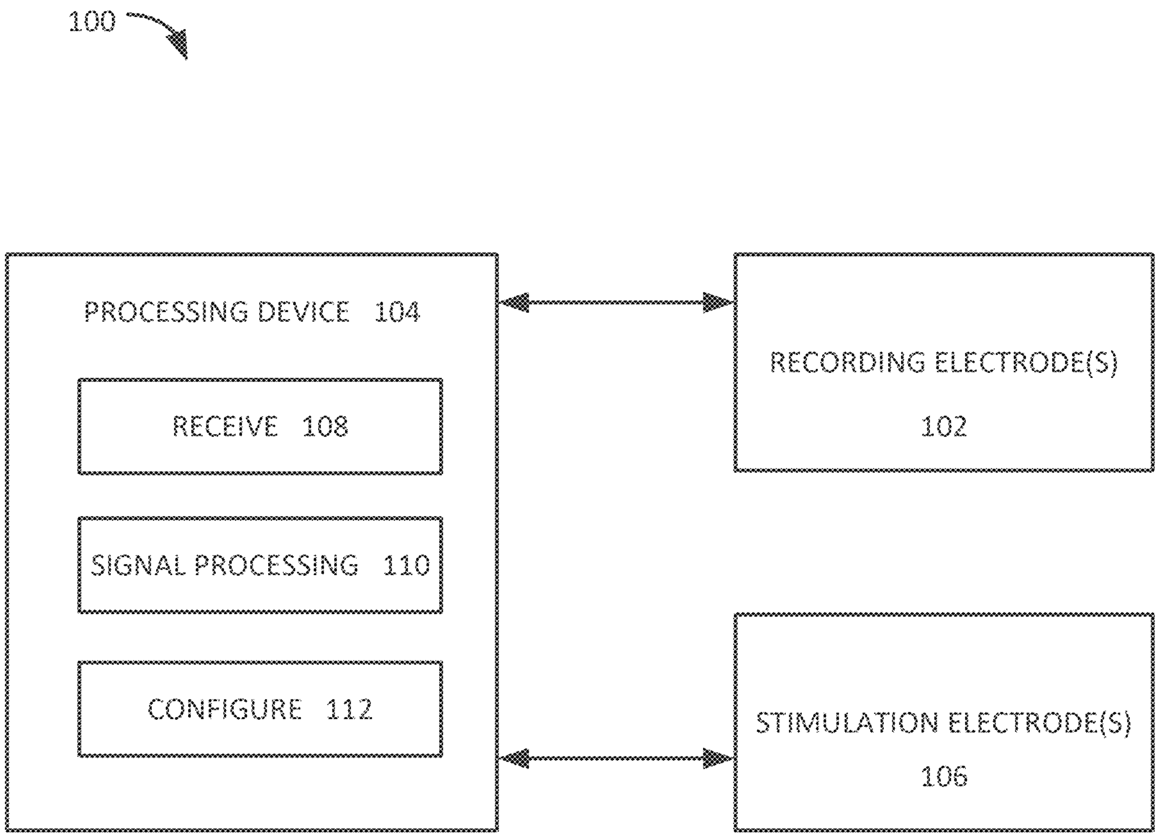
FIG. 1 is a diagram showing a system that can provide closed-loop vagus nerve stimulation for obesity control (and/or treatment of other metabolic/gastric conditions)
Figure 3:
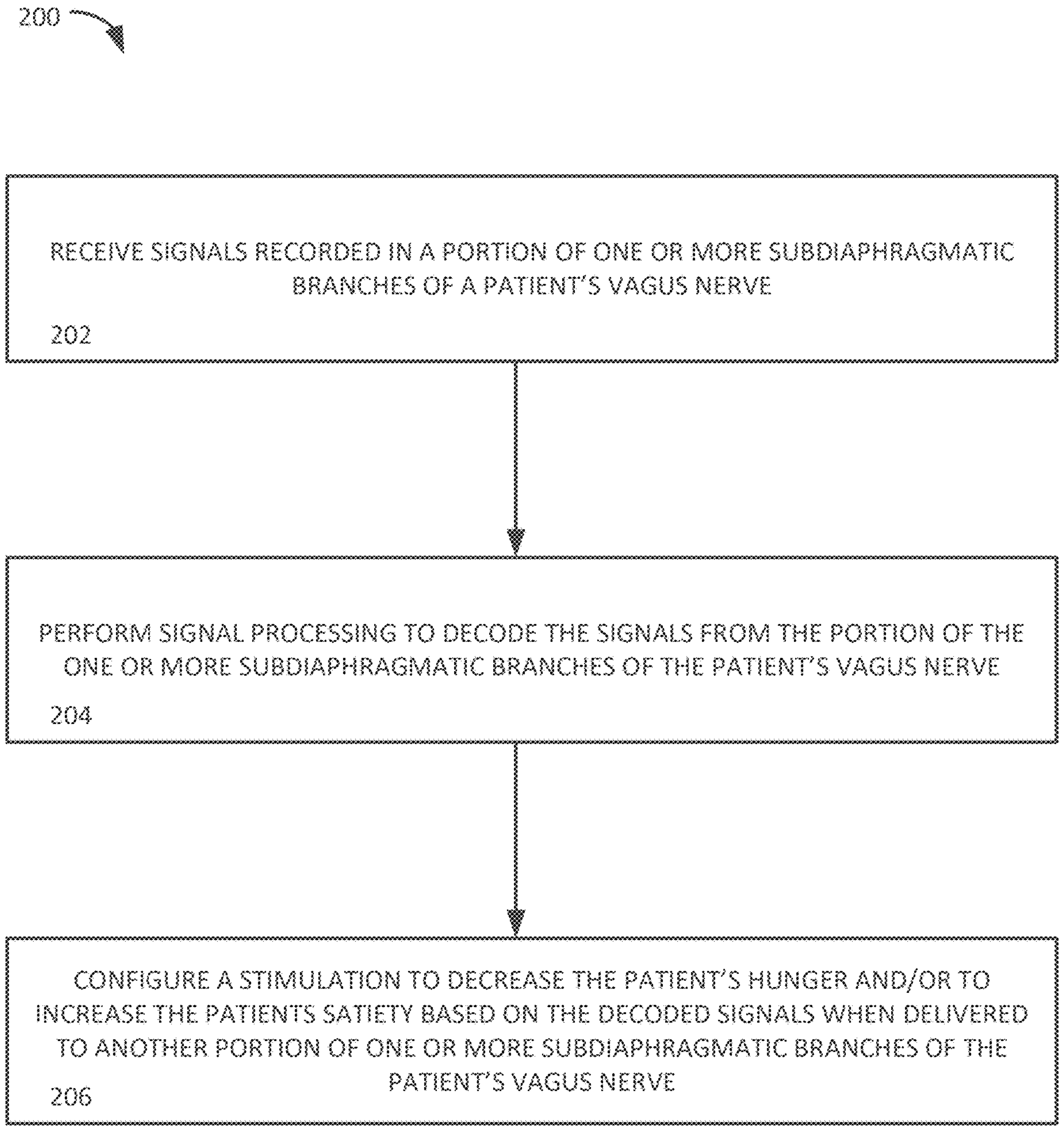
FIGS. 3-4 are process flow diagrams methods for closed-loop vagus stimulation for obesity control (and/or treatment of other metabolic/gastric conditions)
Figure 4:
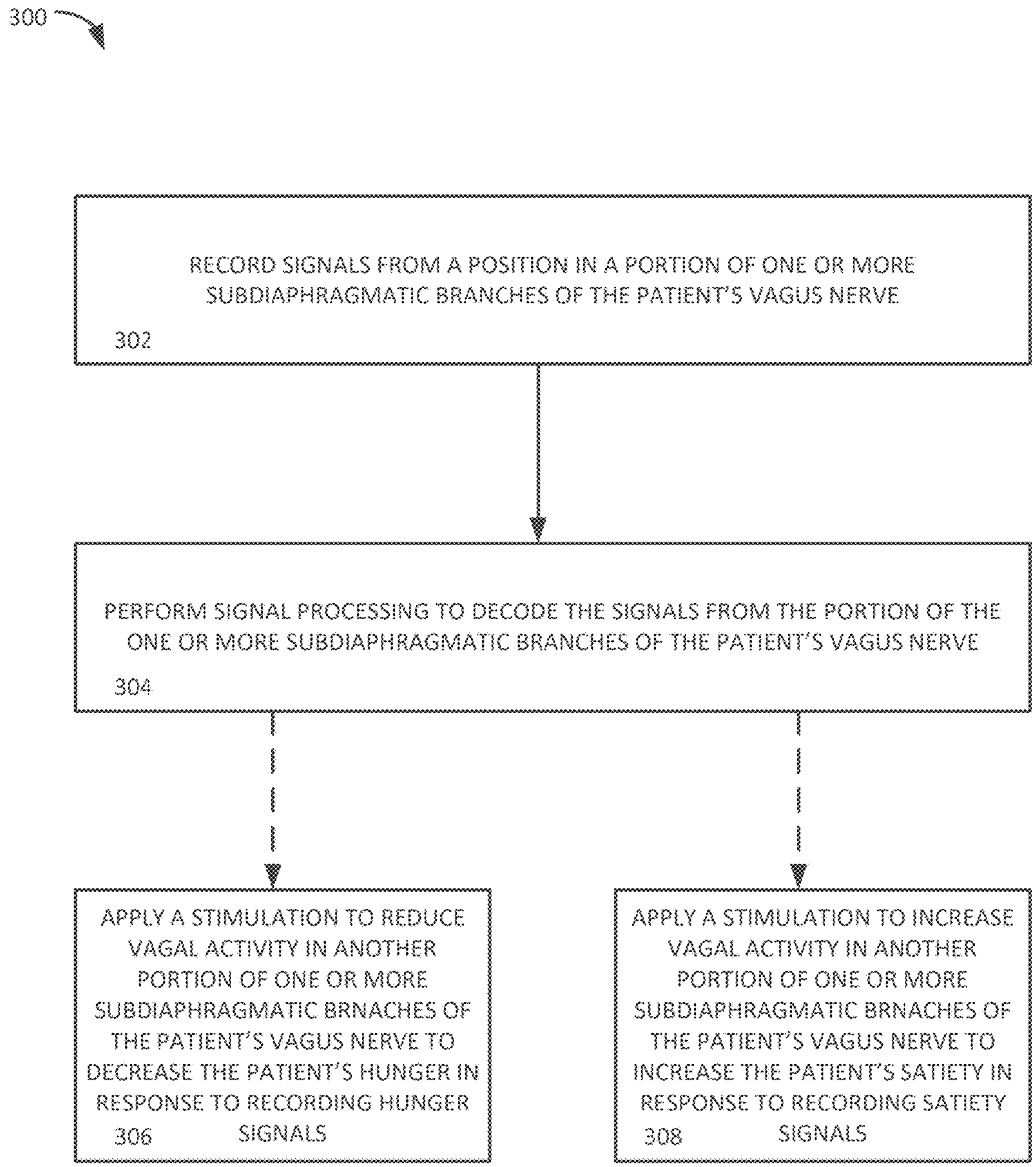

Another aspect of the present disclosure can include methods 200, 300 for closed-loop vagus nerve stimulation for obesity control (and/or treatment of other metabolic/gastric conditions) shown in FIGS. 3 and 4. For example, the other metabolic/gastric conditions may be irritable bowel syndrome/disease, diabetes, or hypertension. The methods can be performed by the system 100 shown in FIGS. 1 and 2.

For purposes of simplicity, the methods are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method, nor is the method necessarily limited to the illustrated aspects. Additionally, at least the processing device 104 is a computer-related entity that includes hardware, including a memory (which is a non-transitory memory) and a processor (e.g., a microprocessor, a computing device, a state machine, a signal processing chip, or the like, and communicates with hardware (e.g., recording electrodes 102 and stimulating electrodes 106) to facilitate the performance the closed-loop system shown in FIGS. 1 and 2. Moreover, the processing device 104 may be implantable or external and linked to internal stimulating 106 and recording 102 electrodes.

A method 200 for closed-loop vagus nerve stimulation for treatment of metabolic/gastric conditions is shown in FIG. 3. At 202, signals recorded (e.g., by recording electrode(s) 102) in a portion of one or more subdiaphragmatic branches of a patient's vagus nerve can be received (e.g., by processing device 104). At 204, signal processing can be performed (e.g., by processing device 104) to decode the signals from the portion of the one or more subdiaphragmatic branches of the patient's vagus nerve. For example, the decoded signals can be used to determine an optimal timing and type of the stimulation. At 206, a stimulation can be configured (e.g., by processing device 104) to decrease the patient's hunger and/or to increase the patient's satiety based on the decoded signals when delivered (e.g., by stimulating electrodes 106) to another portion of one or more subdiaphragmatic branches of the patient's vagus nerve. The stimulation can be configured to reduce vagal activity or increase vagal activity based on the decoded signals. The stimulation is applied to reduce the vagal activity or increase the vagal activity and a signal related to this modulated vagal activity can be recorded by the recording electrodes and fed back into the processing device so that a new stimulation can be configured if need be.

A method 300 for treatment of obesity by delivering a closed-loop stimulation is shown in FIG. 4. At 302, signals recorded (e.g., by recording electrode(s) 102) in a portion of one or more subdiaphragmatic branches of a patient's vagus nerve can be received (e.g., by processing device 104). At 204, signal processing can be performed (e.g., by processing device 104) to decode the signals from the portion of the one or more subdiaphragmatic branches of the patient's vagus nerve. For example, the decoded signals can be used to determine an optimal timing and type of the stimulation. At 306 and 308, a stimulation can be configured (e.g., by processing device 104) to decrease the patient's hunger and/or to increase the patient's satiety based on the decoded signals when delivered (e.g., by stimulating electrodes 106) to another portion of one or more subdiaphragmatic branches of the patient's vagus nerve. For example, at 306 the stimulation can reduce vagal activity when signals related to hunger are received to decrease hunger. In another example, at 308, the stimulation can increase vagal activity when signals related to satiety are received to increase satiety.

In either method 200 or 300, the processor can be trained during a training period to recognize the signals that indicate times of hunger, amount, and length of food intake, and/or satiety feelings after meals. During the training period, the patient can indicate the times of hunger, the amount, and the length of food intake, and/or the satiety feelings after meals. This can help the processing device 104 better recognize/decode the signals.

V. Experimental

Experiment 1

The following experiment shows chronic recording and decoding of activity in the vagus nerve of freely moving animals enabled by the axon-like properties of the CNTY biosensor in both size and flexibility and provides an important step forward in the ability to understand spontaneous vagus-nerve function.

In this study, spontaneous vagal-spiking activity from awake, freely moving rats were continuously recorded for >48 hours up to two weeks after implantation. It is thought that this is the first time this has been successfully demonstrated. The neural-recording data was synchronized with continuous video recording of the subjects. Spike sorting is used to separate semi-distinct spike clusters, which are then correlated to animal behavior identified from the video recordings. Interspike interval distributions are also found to change in response to food intake, presenting another neural feature that can be used to decode spontaneous vagal activity. Several spike clusters that show tuning to animal eating are reported, and the firing dynamics of multiple decoded spike clusters can be used to classify eating compared to drinking, grooming, and resting behaviors.

Materials and Methods

CNTY Electrode Manufacture

Figure 5:
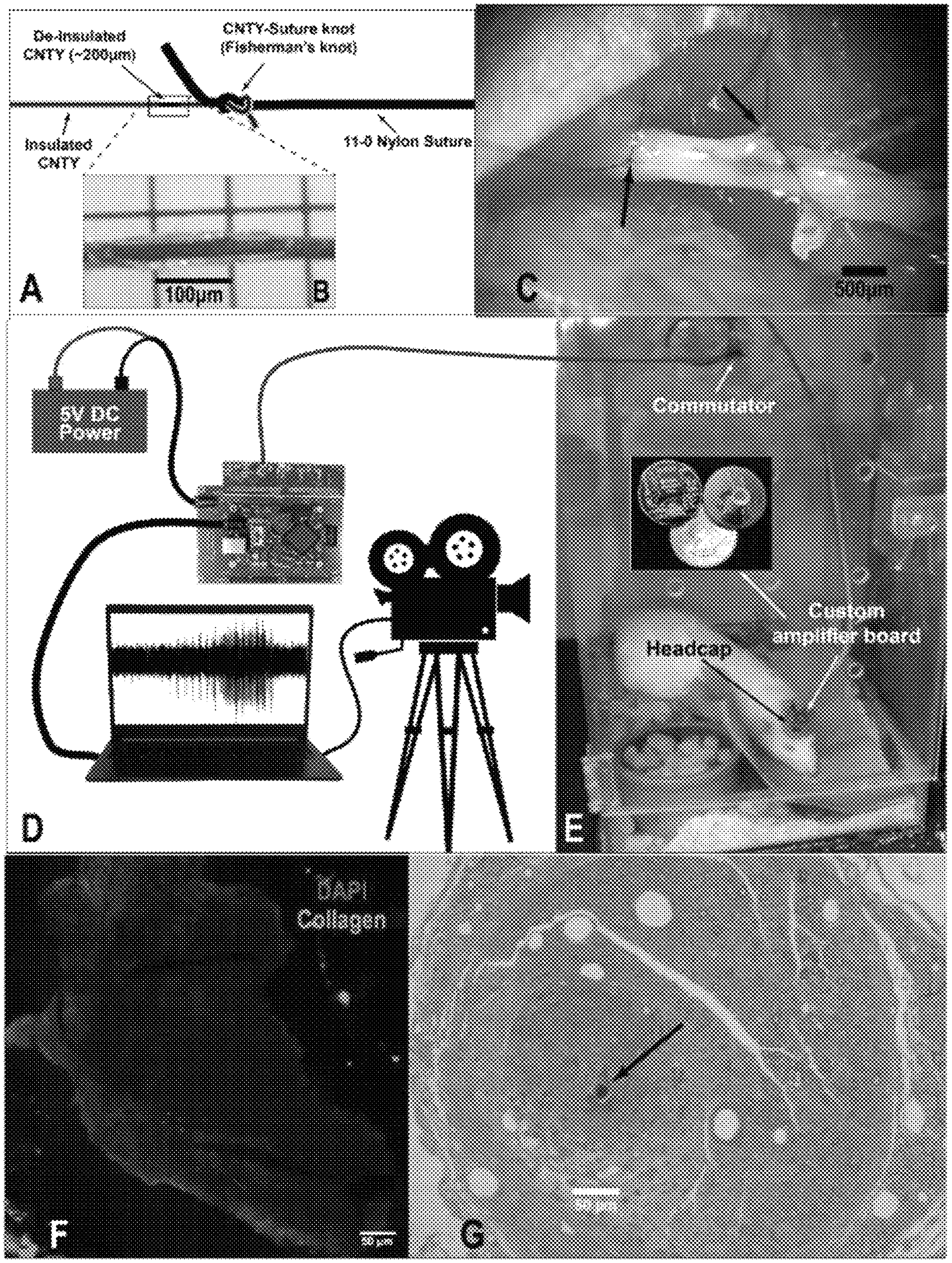
FIG. 5 illustrates electrode implantation, histology, and recording methods for an experiment.

CNT yarns were manufactured at Case Western Reserve University, as described previously. CNTYs were then connected to 35NLT®-DFT® wire (FortWayne Metals, FortWayne, IN, USA) with silver conductive epoxy (H20E, EPO-TEK), creating a CNTYDFT® junction. Dacron mesh and silicone elastomer (MED-4211/MED-4011, NuSil Silicone Technology, Carpinteria, CA, USA) were added to seal the junction, confirmed by measuring the impedance of the junction at 1 kHz in a saline bath. The free end of the CNTY was tied to the end of an 11-0 nylon suture (S&T 5V33) using a fisherman's knot, as shown in FIG. 5, element A. The entire CNTY was coated with parylene-C (5 μm thick vapor deposition coating, SMART Microsystems, Elyria, OH, USA) on a custom rack which masks the suture needle from coating. Then, a small section (~200 μm long) of parylene-C was removed approximately 500 μm behind the CNTY-suture knot using a laser spot welder (KelanC Laser, set to 1 A current, 0.3 ms pulse width, and 300 μm diameter), as shown in FIG. 5, element B. FIG. 5 element C shows the CNTY-suture knot outside of the nerve after implantation. Electrode viability was confirmed by measuring the impedance of the recording site before and after using the laser.

FIG. 5, element A is a diagram of CNTY electrode mated with an 11-0 nylon suture with a fisherman's knot. FIG. 5, element B is a section of CNTY electrode deinsulated by laser. FIG. 5, element C Vagus nerve with two implanted CNTY electrodes. CNTY-suture knots are shown with arrows. FIG. 5, elements D/E are diagrams showing the setup for continuous recording of vagal activity and video for behavior identification. Signals travel from the implants to the headcap connector mounted on the animal's skull, where they are digitized and amplified by the custom amplifier board shown. These signals are then routed through a commutator, which can rotate and allows the animal to move freely without twisting or pulling on the cable. From the commutator, the signals are sent to an USB interface board, which is powered by an external DC-power source and finally sends the signals to a computer, where they are saved and can be viewed in real time. A video camera is manually synced to the vagal recordings. FIG. 5, element F includes fluorescent images showing collagen+ cellular encapsulation of CNTY electrodes implanted in the vagus nerve for seven days. FIG. 5, element G is a toluidine blue-stained nerve section showing encapsulation of a CNTY electrode implanted for two weeks.

Surgery

All surgical and experimental procedures were done with the approval and oversight of the Case Western Reserve University Institutional Animal Care and Use Committee to ensure compliance with all federal, state, and local animal welfare laws and regulations. Electrodes were implanted in male Sprague Dawley rats between 7-12 weeks of age.

To expose the left cervical vagus nerve, a midline incision was made along the neck. The muscles and salivary glands were separated and held in place, revealing the carotid sheath which contains the carotid artery and vagus nerve. The vagus nerve was carefully separated from the carotid artery using blunt dissection and held in slight tension using a glass hook. CNTY electrodes were implanted by sewing the suture through the nerve for ~2 mm, then pulling the suture until the CNTY-suture knot was pulled through. Then, the electrode was pulled back so that the knot sat against the epineurium, ensuring the recording site remained inside the nerve, as shown in FIG. 5, element C. Two electrodes were implanted with ~2 mm separation; the extra suture and needles were cut off after implantation, and the nerve, electrodes, and junctions were covered with ~1 mL of fibrin glue (Tisseel, Baxter International Inc., Deerfield, IL, USA) to help secure the area for recovery. Next, the DFT wires were tunneled from the neck to the back of the skull and soldered to a 5-pin Omnectics connector (Omnetics Connector Corporation MCP-5-SS). The skin on top of the skull was opened, and the connector was fixed on top of the skull with dental cement. The amplifier ground was connected to a screw placed in the skull, which also helps keep the headcap in place. Electrodes were implanted for chronic recording in two animals, and animals were given one week for recovery before recording.

Recording

Recordings were carried out continuously in awake, behaving animals for 56 and 40 hours (Rat 1 and 2, respectively). A custom-built PCB with an Intan RHD2216 recording chip was attached to the headcap connector, which was secured to the animal with a 3D-printed locking mechanism and attached to a PlasticsOne® (Roanoke, VA, USA) commutator, allowing the rat to move around the cage without tangling or pulling on the connector cable. Input signals were routed to eight amplifier channels, using 8-channel hardware averaging to decrease amplifier noise. Output from the amplifier board was run through the commutator into an Intan RHD USB Interface board (Intan part #C3100), which is powered by an external battery supplying 5V DC power. Signals are then routed to a computer where they are saved for offline analysis and can be viewed in real time.

Neural recordings were sampled at 20 kHz with a 5 kHz low-pass filter. Recordings were started around 10 AM (approximately four hours after the start of the light cycle). During ENG recording, a video camera was used for simultaneous video recording. The camera was equipped with an infrared light and infrared sensor, allowing for filming even during the dark cycle. The camera was connected to the recording computer and manually synced to the recording. A diagram of the recording setup can be seen in FIG. 5, elements D, E.

Signal Processing

Figure 11:
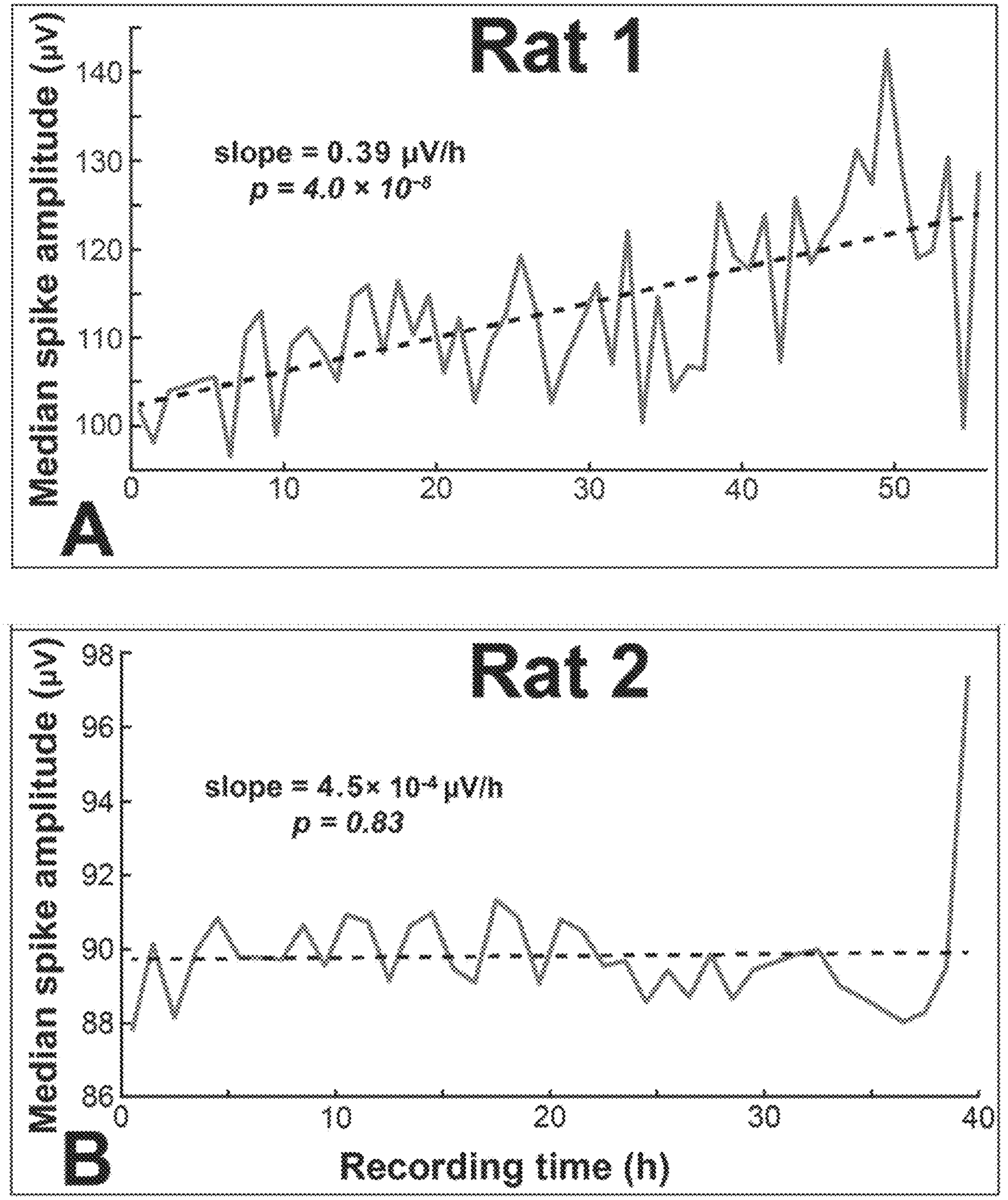
FIG. 11 illustrates median spike amplitudes over time for subjects 1 and 2 of the experiment.

ENG data were imported into MATLAB, where they were further processed. ENG was band-pass filtered from 500-5000 Hz to minimize interference from EMG, ECG, or other possible sources. The filter bandwidth was kept relatively wide to minimize distortion of spike waveforms. Spikes were detected and sorted into clusters using the UltraMegaSort2000 software in MATLAB, using a threshold of eight times the RMS of baseline. Spike waveforms (3 ms long) were transformed into the principal component space, and principal components accounting for 95% of the total waveform variance were used for spike clustering. Spike clustering was done using k-means clustering of spike waveform principal components, with a maximum of k=256 clusters. Using the UMS2000 software, clusters were further analyzed for better separation and exclusion of artifacts. First, outliers were removed if they had a z-score greater than 500 on the $x^2$ distribution of distance to the cluster center. Clusters were removed from analysis if the spike waveform contained a second, larger threshold crossing (i.e., removing of spikes which were detected twice due to threshold-crossing of the spike tail). Clusters were also removed if spike width was less than 0.3 ms and amplitude was greater than 1 mV (presumed recording artifacts) or if spike width was greater than 2 ms. Spike waveform values were used to calculate spike amplitudes (difference between the maximum and minimum voltage values) and the spike RMS. Spike-cluster-firing timings were also used to calculate cluster-firing rates and interspike intervals (ISI). Average spike amplitudes over time are shown in FIG. 11, and spike RMS was used to calculate average SNR, shown in FIG. 12. Animal behaviors (eating, drinking, grooming, and resting) were identified via video recording. The overall data processing and analysis workflow is diagrammed in FIG. 6, where vagal ENG and video are recorded simultaneously from freely moving rats; spike sorting is used to decode spike metrics, which are analyzed with respect to animal behaviors identified from the video.

Histology

Toluidine blue staining: the image shown in FIG. 5, element G was obtained from an implanted nerve which was fixed, sectioned, and stained with toluidine blue. Two weeks after implantation, animals were perfused with 1.25% glutaraldehyde, 1% formalin, and 0.1 M phosphate buffer. This fixative solution is approximately 640 mOsM/kg. Animals were injected with 0.2-0.5 mL of 1% procaine at 37° C. through the left ventricle. Followed by 200 mL of the fixative solution perfused at 37° C. using a variable speed peristaltic pump. After completing the perfusion process, the vagus nerve was dissected at the implant location. The complete nerve section was transferred into a postfixative solution (1% osmium tetroxide in 100-mM phosphate buffer) for two hours at room temperature before being transferred to 4° C. Following postfixation, the nerve tissue was dissected in 1-mm-long pieces and embedded in an epoxy resin. Sections (0.7 m) were cut from the epoxy blocks using a diamond knife (DiATOM) microtome. Toluidine blue (1% toluidine blue and 2% borate) was used to stain the nerve axons.

Fluorescent staining: the image shown in FIG. 5, element G was obtained from an implanted nerve which was optically cleared using the CLARITY protocol. Seven days after implantation, the vagus nerve was extracted and immediately placed into hydrogel monomer solution. The sample was passively cleared and stained with a collagen antibody, as described previously by this group. DAPI staining was done by placing the sample in VectaShield with DAPI (Vector Laboratories) on a glass-bottom petri dish (Ted Pella, Inc., Redding, CA, USA). Samples were imaged on a Leica SP8 gSTED Super-Resolution Confocal microscope (Leica Microsystems, Wetzlar, Germany).

Figure 6:
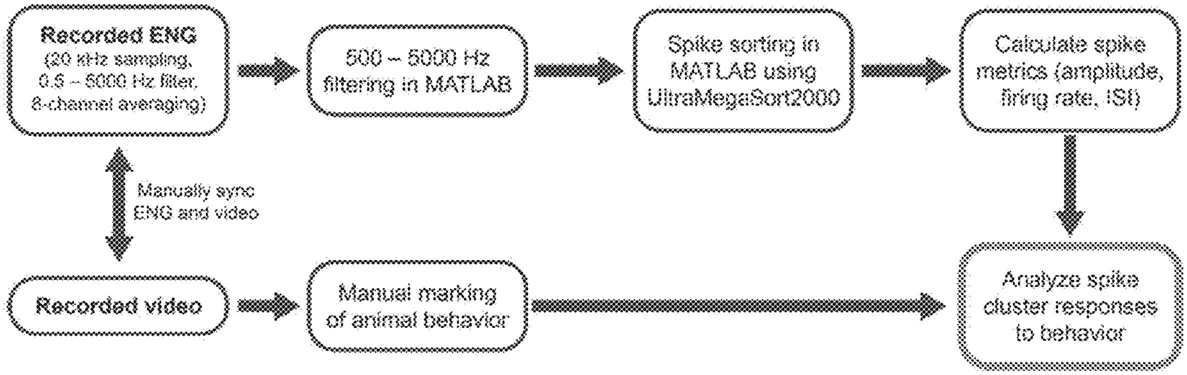
FIG. 6 is a diagram of data processing and analysis workflow of the experiment.

Statistical Methods

Where relevant, results are reported as mean±standard deviation. Average spike waveforms in FIG. 6 are shown with shaded areas representing the 95% confidence interval. Overall spike-firing rate, median spike amplitudes, and average spike SNR over time were fitted with a linear regression to determine if the slope was different from zero, with slopes and p-values shown in FIG. 6, and FIGS. 11 and 12. Spike clusters were grouped based on their response to eating, and firing rate changes before, during, or after eating for each group were compared to baseline group firing rates using a one-sample t-test, with a significance level of 0.01 and a Bonferroni correction ($\alpha=5.6\times10^{-4}$), as shown in Table 1. ISI distributions of the before, during, and after eating periods were compared to noneating periods using a two-sample Kolmogorov-Smirnov test, with a significance level of 0.01 and a Bonferroni correction for the number of tested distributions ($\alpha=2.2\times10^{-5}$, Table 2). All tests performed were two tailed.

TABLE 1

Firing rates of cluster groups relative to eating. Sorted clusters are separated into five cluster groups based on their response to eating. Table 1 shows the number of clusters of each group recorded in both animals and the behavior of those cluster groups before, during, and after eating: up arrow means an increased firing rate, dash means no change in firing rate, and down arrow means a decreased firing rate for the cluster group.

| Cluster Group | Rat 1 | Rat 2 | Before Eating | During Eating | After Eating |
|---|---|---|---|---|---|
| Group I | 19 | 0 | ↑ p << 0.0001 | ↑ p << 0.0001 | ↑ p << 0.0001 |
| Group II | 13 | 13 | ↑ p << 0.0001 | — p = 0.024 | ↑ p << 0.0001 |
| Group III | 24 | 0 | ↑ p << 0.0001 | ↓ p ≤ 0.001 | ↑ p << 0.0001 |
| Group IV | 0 | 59 | ↑ p << 0.0001 | ↑ p << 0.0001 | — p = 0.95 |
| Group V | 0 | 1 | ↑ p << 0.0001 | — p = 0.0093 | ↓ p << 0.0001 |

TABLE 2

Differences in ISI distributions for before, during, and after eating periods, compared to non-eating periods, for all clusters which had at least one group with a significant change. Cluster groups are shown for each cluster (see Table 1), and non-significant p-values are not shown.

| Cluster Number | Cluster Group | Before Eating | During Eating | After Eating |
|---|---|---|---|---|
| 1.8 | II | $9.4\times10^{-45}$ | NS | $1.4\times10^{-27}$ |
| 1.14 | II | $3.2\times10^{-10}$ | $2.1\times10^{-5}$ | $7.3\times10^{-7}$ |
| 1.18 | II | $6.9\times10^{-13}$ | NS | NS |
| 1.20 | II | $5.7\times10^{-11}$ | NS | NS |
| 1.21 | II | $9.9\times10^{-11}$ | NS | NS |
| 1.28 | II | $1.9\times10^{-9}$ | NS | NS |
| 1.29 | II | $4.4\times10^{-9}$ | NS | NS |
| 1.30 | IV | $2.5\times10^{-6}$ | NS | NS |
| 1.52 | IV | $4.0\times10^{-10}$ | NS | NS |
| 1.56 | IV | $6.4\times10^{-13}$ | $8.2\times10^{-9}$ | $1.4\times10^{-11}$ |
| 2.10 | IV | NS | $3.6\times10^{-11}$ | NS |
| 2.11 | IV | NS | $4.9\times10^{-8}$ | NS |
| 2.12 | IV | NS | $2.4\times10^{-8}$ | NS |
| 2.13 | IV | NS | $5.1\times10^{-7}$ | NS |
| 2.16 | IV | NS | $6.3\times10^{-6}$ | NS |

TABLE 2-continued

Differences in ISI distributions for before, during, and after eating periods, compared to non-eating periods, for all clusters which had at least one group with a significant change. Cluster groups are shown for each cluster (see Table 1), and non-significant p-values are not shown.

| Cluster Number | Cluster Group | Before Eating | During Eating | After Eating |
|---|---|---|---|---|
| 2.18 | IV | NS | $9.6 \times 10^{-10}$ | NS |
| 2.21 | IV | NS | $8.8 \times 10^{-9}$ | NS |
| 2.24 | IV | NS | $3.9 \times 10^{-6}$ | NS |
| 2.30 | IV | NS | $3.1 \times 10^{-6}$ | NS |
| 2.31 | IV | NS | $1.0 \times 10^{-5}$ | NS |
| 2.33 | IV | NS | $7.7 \times 10^{-12}$ | NS |
| 2.34 | IV | NS | $5.5 \times 10^{-7}$ | NS |
| 2.37 | IV | NS | $2.3 \times 10^{-10}$ | NS |
| 2.40 | IV | NS | $2.8 \times 10^{-10}$ | NS |
| 2.42 | IV | NS | $2.0 \times 10^{-5}$ | NS |
| 2.43 | IV | NS | $8.2 \times 10^{-6}$ | NS |
| 2.58 | IV | NS | $1.7 \times 10^{-5}$ | NS |
| 2.73 | IV | NS | $2.6 \times 10^{-6}$ | NS |

Results

CNTY Electrodes Record Stable Spikes from Freely Moving Animals

Figure 7:
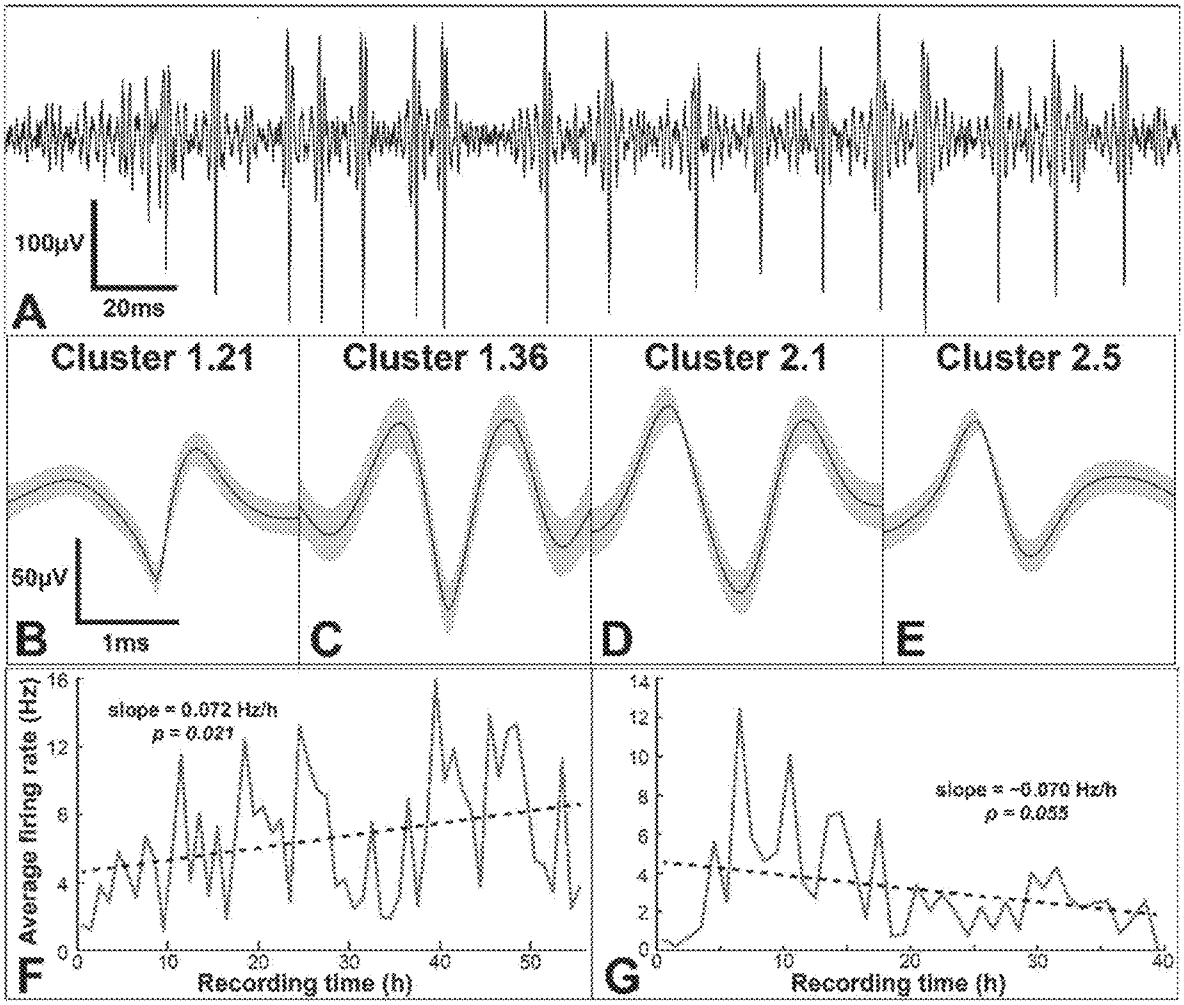
FIG. 7 illustrates spontaneous spikes of vagal activity recorded in freely moving subjects, including filtered and clustered data.
Figure 12:
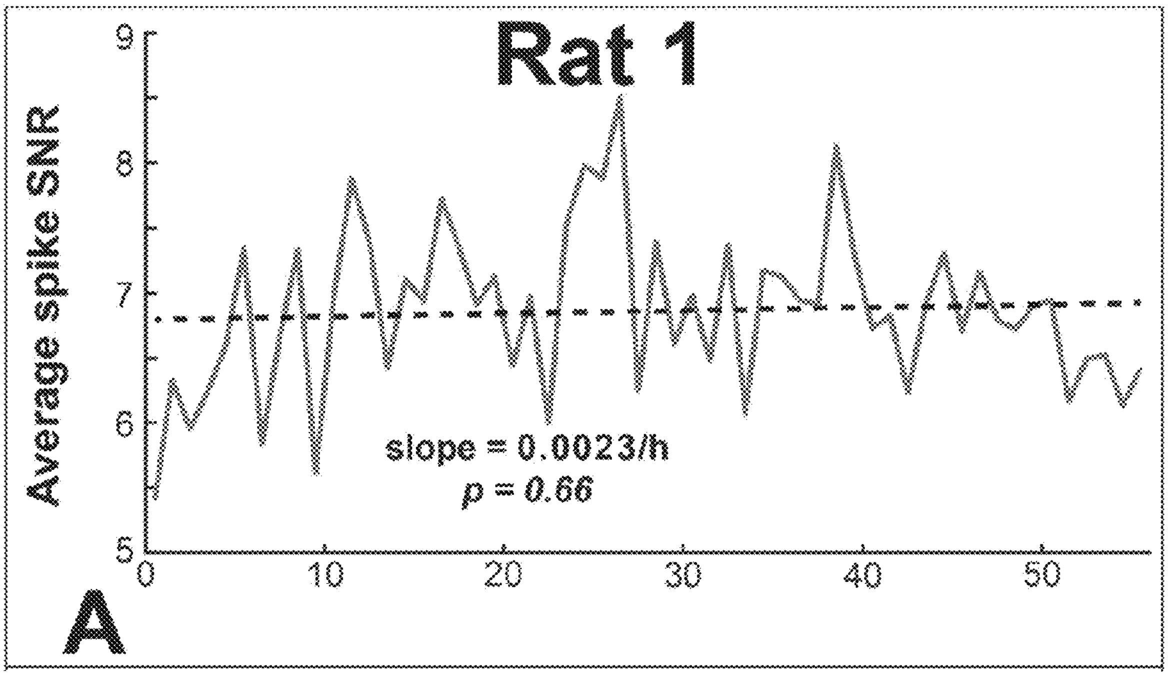
FIG. 12 illustrates average spike signal to noise ratio (SNR) for subjects 1 and 2 of the experiment.
Figure 12:
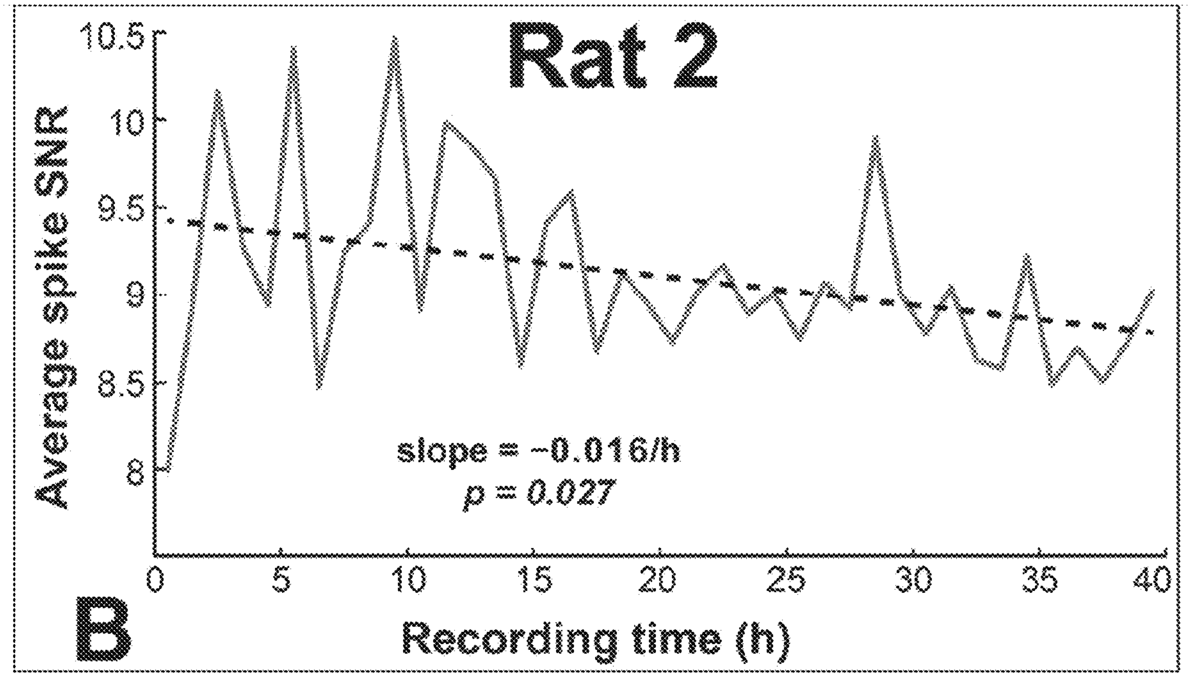

It has previously been shown that CNTY electrodes can record spikes from the glossopharyngeal and vagus nerves in anesthetized rats and can be used to measure vagal tone in freely moving animals. Here, a novel continuous chronic-recording setup is demonstrated (shown in FIG. 5, elements D,E) to record unanesthetized spiking activity which can be sorted into semi-distinct clusters. A total of four electrodes were implanted, two each in the left cervical vagus nerves of two rats, with an average impedance of 11.7±6.5 KW at the time of implantation (measured at 1 kHz). Further measurements of CNTY electrode impedances for long-term implants have been published previously. FIG. 7, element A shows an example of filtered ENG with several recorded spikes, and FIG. 7, elements B-E show several example spike clusters from two animals. A total of 132 spike clusters were identified (56 in Rat 1, and 76 in Rat 2). Clusters are referred to as RatNumber.ClusterNumber (e.g., Cluster 1.21 is Cluster 21 from Rat 1). Average peak-to-peak amplitude of recorded spikes was 152±97 μV for Rat 1 and 180±162 μV for Rat 2. Spike SNR, defined as the average RMS of the spike waveforms compared to the RMS of the baseline, was 7.0±4.9 for Rat 1, and 9.1±5.3 for Rat 2. This is significantly larger than published SNR for acute recording with either the TIME or the LIFE electrodes. Furthermore, median spike amplitude for all recorded spikes was stable over the recording time for Rat 2 and slightly increased over time for Rat 1, as shown in FIG. 11. Overall spike-firing rates were also consistent over the recording periods for both animals: FIG. 7, elements F and G show the average firing rates for each hour of recording, with least-squares regression lines showing no significant change in firing rate over time. Similarly, average spike SNR was stable over the recording time for both animals, as shown in FIG. 12. Thus, it is possible to continuously record vagal spikes which have stable amplitude, SNR, and firing rates over time.

Spike Clusters' Activity Is Correlated with Eating

Identifying the function of spontaneous spikes in freely moving animals is important to understanding how vagal fibers modulate their activity during normal animal behavior. Given the high ratio of gastric afferents in the vagus, most vagal spiking is involved with gastric signaling.

Figure 8:
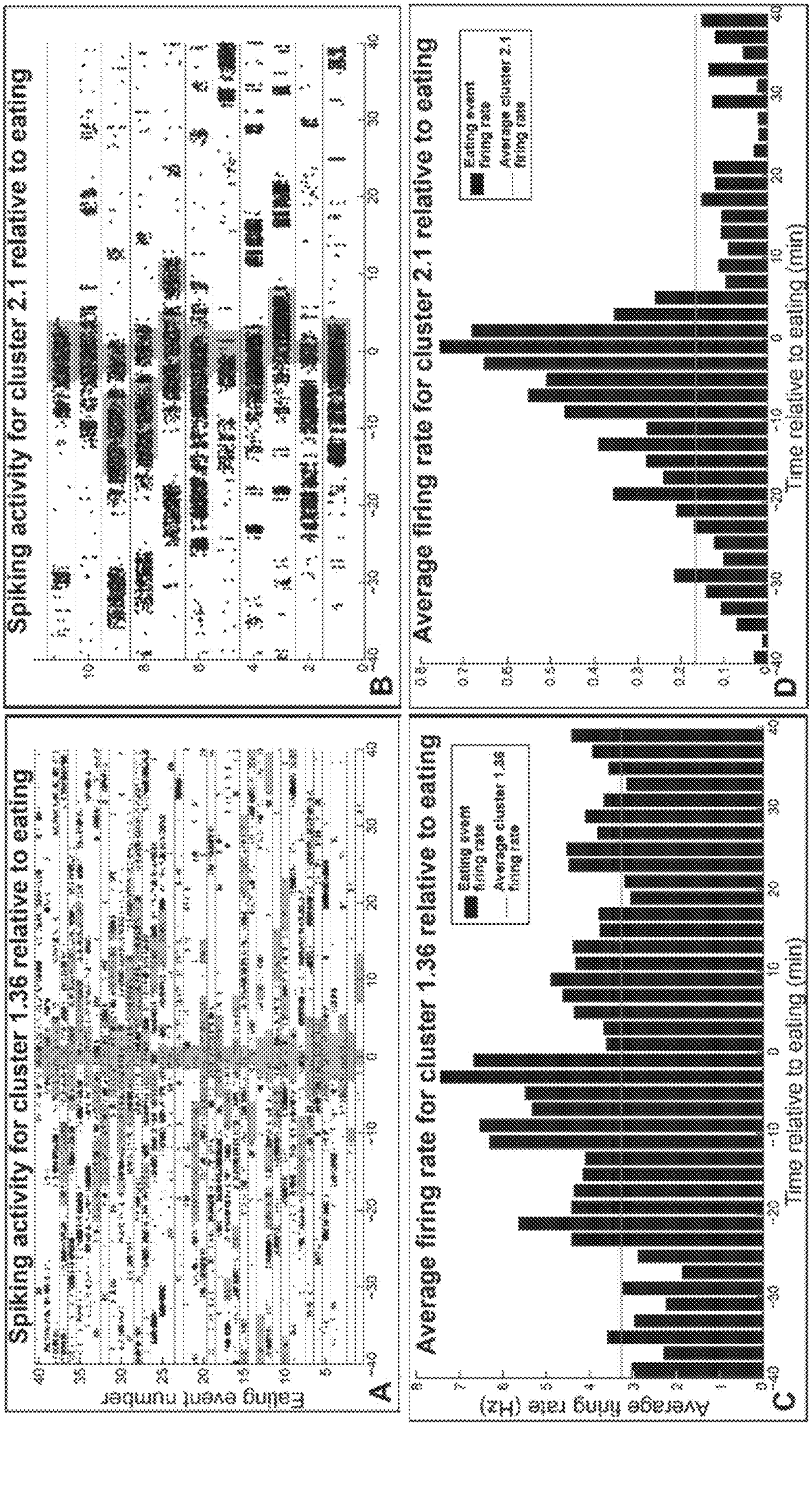
FIG. 8 illustrates example spiking activity related to eating as raster plots.

After animal-eating times were identified from video recordings, they were compared to the firing rates of individual spike clusters. In both animals, several clusters show a significant increase in firing rate that occurs <25 min before eating. Some clusters also had increased or decreased firing that occurred during eating, while others had increased firing that occurred <10 min after eating. FIG. 8, elements A and B show raster plots for one such spike cluster from each animal, with each row representing one eating event (shown by the shaded grey area). FIG. 8, elements C and D show the average firing rate of these clusters relative to the eating events, along with the overall average firing rate for each cluster. Cluster 1.36 (see FIG. 8, elements A and C) had higher-than-average activity in the 25 min before eating, and higher-than-average activity in the 10 min following eating, with no change occurring during food consumption. Similarly, the firing rate of Cluster 2.1 is increased before and during eating, and unchanged after eating.

Many clusters exhibited a mix of behaviors, showing firing rates before, during, or after eating that were significantly different from baseline activity ($p<0.01$ with Bonferroni correction). To analyze cluster behavior related to eating, clusters were sorted into groups based on their firing rate response before eating (from 25 min before, until the start of eating), during eating, and after eating (end of the eating event, until 10 min after eating). These data are summarized in Table 1 for both rats, which show how the cluster-firing rates changed for each group and the number of clusters from each animal which make up each group. The table shows the direction of change and associated p-value for the changes in firing rate of each group in the different eating-related periods (sum of the spiking activity in all clusters within a group compared to the baseline firing activity for the clusters in that group). Only 3 of the 132 recorded clusters did not showing any significant tuning to eating behavior. While specific spiking correlations are unique to each subject, they are consistent within each animal, and FIG. 7 and Table 1 show that spike clusters that exhibit firing rate changes before, during, and after eating can be identified in both subjects.

Spike Cluster Interspike Intervals Show Changes in Bursting Related to Eating

Figure 9:
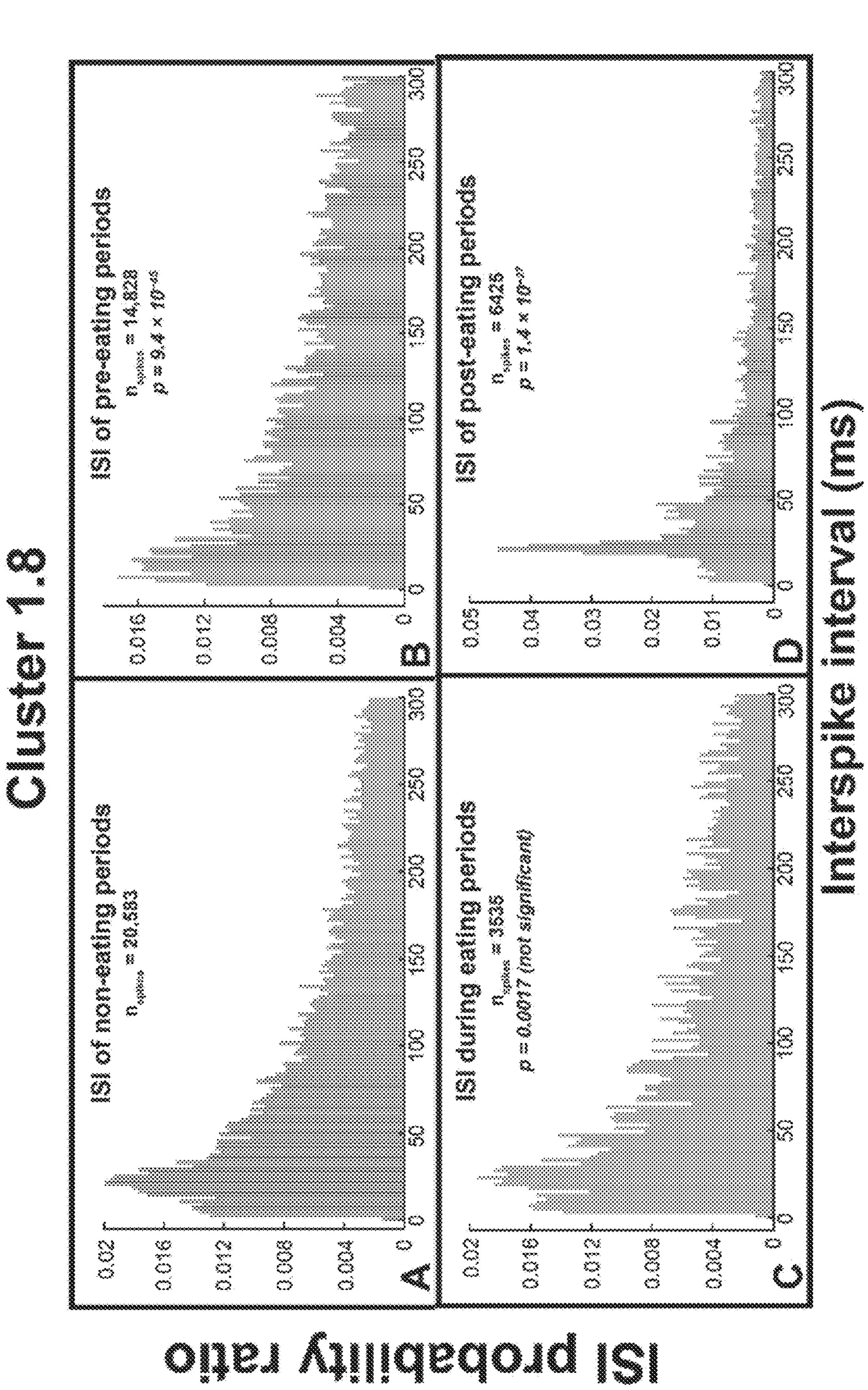
FIG. 9 illustrates interspike interval histograms for experimental Cluster 1.8.

Spikes are often observed exhibiting bursting behavior, where fibers tend to fire at specific frequencies. Bursting behavior can be seen in FIG. 8, elements A and B, where spikes appear in clumps. To quantify bursting, spike cluster interspike intervals (ISIs) were calculated for noneating, pre-eating, during eating, and post eating time windows. Eating-related distributions were compared to noneating distributions using a two-sample Kolmogorov-Smirnov test and were plotted in a histogram. FIG. 9 shows ISI distributions for noneating, pre-eating, during eating, and post eating periods for one example cluster (Cluster 1.8, which is part of Group II and has increased activity before and after eating). In FIG. 9, element A, the peak ISI of this cluster during noneating times is around 21 ms or a 48 Hz firing rate. However, in the 25 min before eating, this distribution shifts to the left, peaking instead at 7 ms or 143 Hz, signifying an increase in the bursting firing rate before eating. In the 10 min following eating, the bursting rate returns to the noneating value, though the ISI peak is more pronounced, meaning that bursting is a more prevalent spike behavior after eating. After finishing eating, a secondary peak was observed at around 47 ms (21 Hz). During eating, the ISI distribution is not significantly different from noneating; thus, the bursting activity of Cluster 1.8 is changed before and after, but not during, eating behavior (see FIG. 9, elements A-D). In total, 10 clusters in Rat 1 and 18 clusters in Rat 2 demonstrated changes in ISI distribution related to eating.

These data are summarized in Table 2 which shows p-values comparing noneating and eating-related ISI distributions for any cluster which showed a significant change. The 18 clusters in Rat 2 only showed a change in ISI distribution during eating, with no changes either before or after. The 10 clusters in Rat 1 each showed changes before eating, while some also had a significantly different ISI distribution during or after eating as well. FIG. 9 and Table 2 show that some of the spike clusters which are tuned to eating are observed to change bursting activity related to eating, though not all the clusters which show changes in overall activity have altered ISI/bursting behavior.

Figure 10:
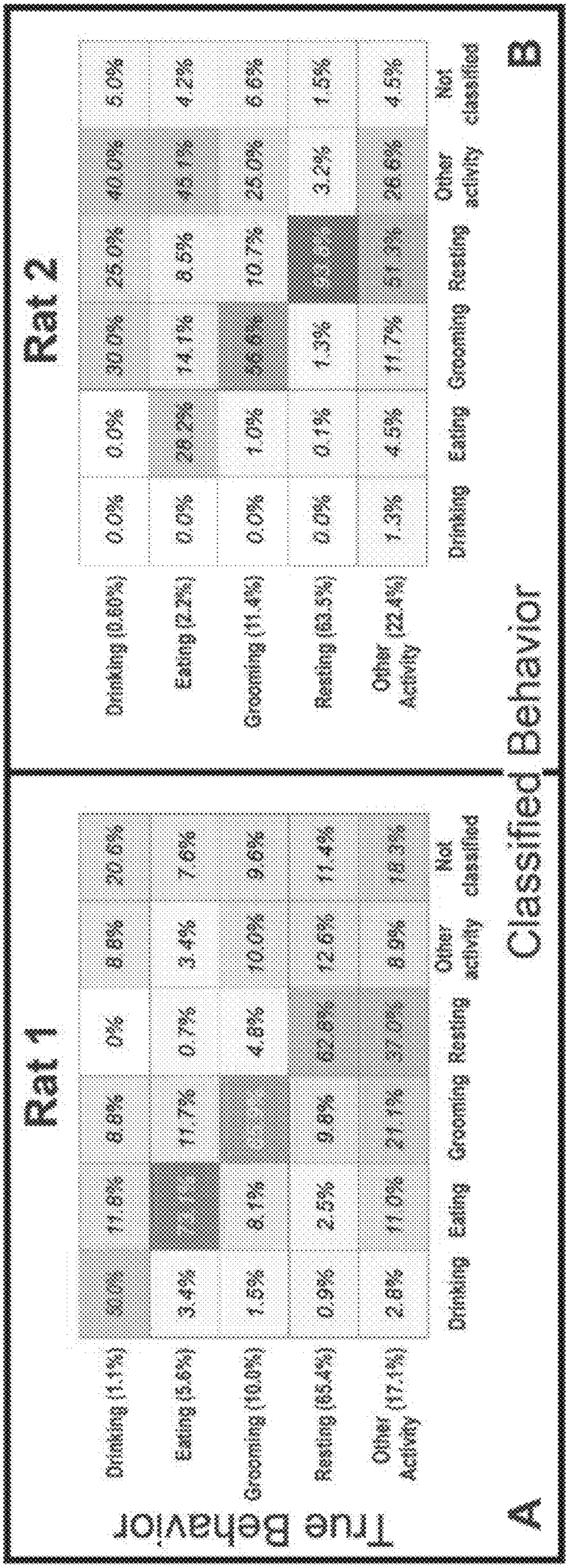
FIG. 10 shows confusion matrices for classifying animal behavior based on spike firing rates for subjects 1 and 2 of the experiment.
Figure 13:
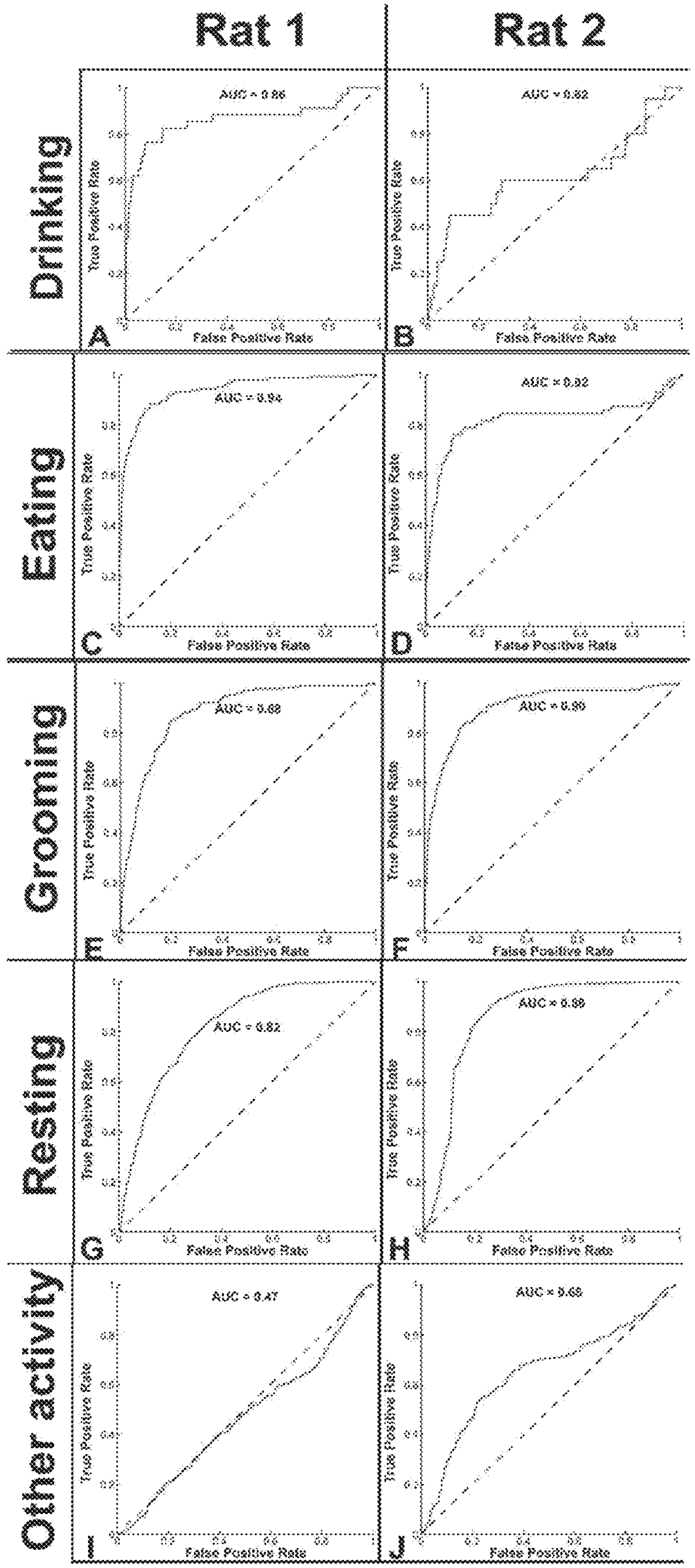
FIG. 13 illustrates receiver operating characteristic (ROC) curves and area-under-the-curve (AUC) values used to assess performance of a multinomial logistic regression model to classify animal behaviors based on spike cluster firing rates with dotted lines showing the expected ROC curve for a random classifier.

Spike-Cluster-Firing Rates Can Be Used to Classify Eating Compared to Other Behavior In addition to showing that individual spike clusters are correlated with food intake, it was also examined whether spike-firing rates are sufficient to classify the times during which the animal is eating, compared to other behaviors, such as drinking, grooming, and resting. A multinomial logistic regression model was constructed, with behaviors and spike-cluster-firing rates averaged over 30 s. The model uses firing rates from each of the recorded clusters, as well as firing rates during peak delayed or preceding correlations with eating. The models were trained on the first ⅔ of recording data and tested on the final ⅓ of recording data. FIG. 10 shows the confusion matrices for both animals, which show the performance of the model for classifying behavior with a probability threshold of $\pi=0.5$ for classification. Percentages on the y-axis show the amount of time spent doing each behavior as a percentage of total recording time. In Rat 1, the model was able to classify eating most accurately, with a 73.1% accuracy. In Rat 2, the model performed best at classifying resting, with a 93.8% accuracy. Additionally, plotting the receiver operating characteristic (ROC) curves and the associated areas under the curve (AUC) in FIG. 13 shows that both models performed better than random chance for almost all behaviors (the only exception being classifying other activity in Rat 1). Overall, these results show that the firing rates of spontaneous vagal spikes sorted into clusters are sufficient to classify eating behavior in freely moving animals.

Experiment 2

The autonomic nervous system is a vital part of regulating homeostasis and overall health. The vagus nerve is the largest autonomic nerve, serving to both sense and control internal organ function. This has led to a variety of neuromodulation therapies targeting the vagus nerve for treatment of chronic diseases, though with somewhat mixed results. Many studies of the vagus nerve focus on the effects of the efferent vagal fibers, with heart rate variability and "vagal tone" chief among them. However, as many as 80% of the fibers in the vagus are afferent, with a majority coming from the gut. Thus, a greater analysis of the behavior of afferent vagal fibers and their impact on chronic health and disease is important, both for improvement of current therapies, and for the development of new therapies. Recent advancement in chronic recording from small peripheral nerves allows for long-term recording from awake, non-anesthetized rats and investigation of spontaneous vagal signals. In this study, spontaneous vagal firing is used to classify several animal behaviors Methods Carbon nanotube yarn (CNTY) electrodes were prepared as described previously1. Two CNTY electrodes were implanted in the left cervical vagus of a 10-week old male Sprague Dawley rat, attached to a connector mounted on the skull. After a two-week recovery, vagus nerve ENG was recorded for 72 consecutive hours with simultaneous video recording. Spike detection and classification was performed using the UltraMegaSort2000 software in MATLAB2. Artifacts, outliers, and clusters with fewer than 2000 spikes during the 72-hour period were removed from the analysis. Several rat behaviors were classified based on the recorded video: eating, drinking, resting, grooming, and other activity. Cluster spike rates and rat behaviors were averaged in 30-second time windows. Then, the mutual information between cluster firing rates and classified behaviors were calculated with varying delays from −1 hour to +1 hour. The first 48 hours of data were used to train a multinomial logistic regression model, with cluster firing rates and peak delayed firing rates found from mutual information analysis used as input variables. The model was then fed the last 24 hours of data, generating a list of classification probabilities for each behavior state. Probabilities greater than 0.5 were categorized and compared to the behaviors classified from recorded video.

Figure 14:
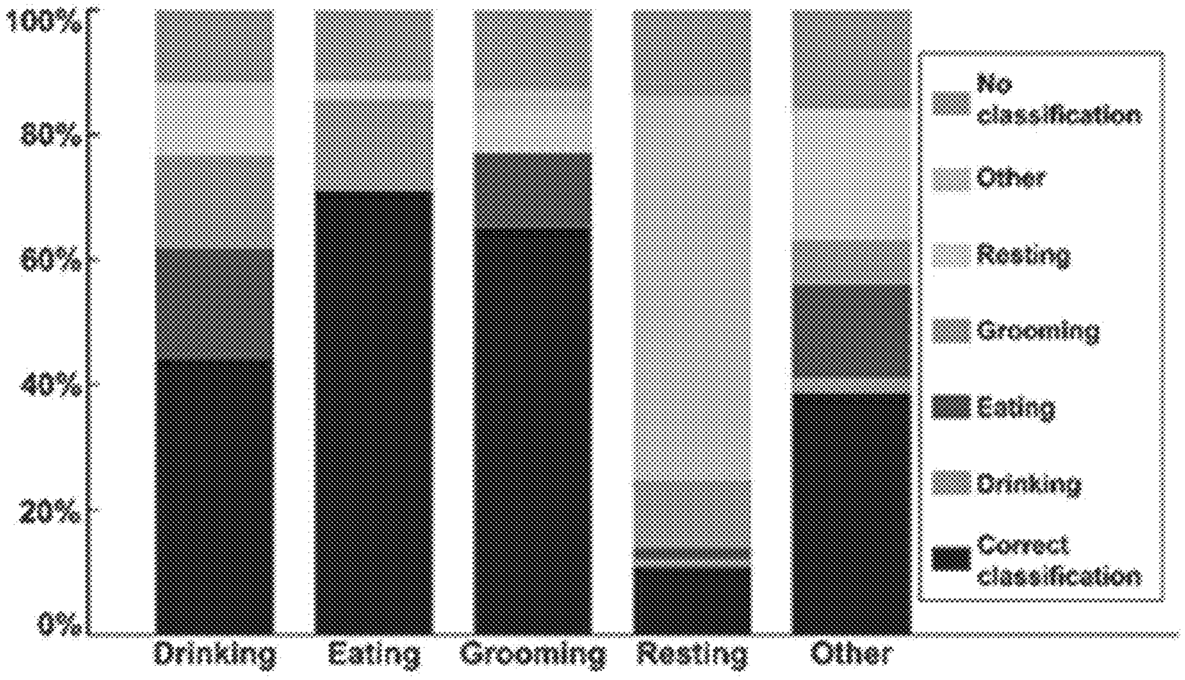
FIG. 14 illustrates accuracy of multinomial logistic regression for classification of animal behavior. Bottom section of each bar (in black) represents the percentage of correct classifications, while the stacked bars represent the modes of incorrect classification.

Results 56 spike clusters were identified which matched the criteria designated above. Of these clusters, 7 exhibited a maximum mutual information occurring with a 10-13 minute delay after eating. An additional 3 clusters showed a maximum mutual information occur-ring with either a positive or a negative time delay compared to drinking (−2.5, −5, and +3.5 minutes). Thus, 66 total input variables were used to create the multinomial logistic regression. FIG. 14 shows the classification accuracy (and errors) of the regression for classification of animal behavior on the last 24 hours of data. The bottom sections of each bar show the percentage of correct classifications for each behavior, with stacked bars representing the modes of incorrect classification. The regression was most effective at classifying eating, with a 71% accuracy.

From the above description, those skilled in the art will perceive improvements, changes, and modifications. Such improvements, changes and modifications are within the skill of one in the art and are intended to be covered by the appended claims. All patents, patent applications, and publications cited herein are incorporated by reference in their entirety.

What is claimed is:

1. A system comprising:

one or more implantable recording electrodes configured to be implanted within a patient's body to record vagal activity signals from a portion of one or more subdiaphragmatic branches of a patient's vagus nerve;

an external processing device coupled to the one or more implantable recording electrodes and one or more implantable stimulating electrodes and configured to receive user inputs, the processing device further configured to:

during a training period:

receive one or more user inputs indicating times of hunger, amount and length of food intake, and/or satiety feelings after meals of the patient and the vagal activity signals from the portion of the one or more subdiaphragmatic branches of the patient's vagus nerve, and match at least a portion of spike clusters of the vagal activity signals with each of the times of hunger, amount and length of food intake, and/or satiety feelings after meals; and after the training period;

receive the vagal activity signals from the portion of the one or more subdiaphragmatic branches of the patient's vagus nerve, perform signal processing to decode the vagal activity signals from the portion of the one or more subdiaphragmatic branches of the patient's vagus nerve into a hunger, eating, and/or satiation event based on the match, and configure a stimulation of an optimal type and timing based on the hunger, eating, and/or satiation event to decrease the patient's hunger and/or increase the patient's satiety; and the one or more implantable stimulating electrodes configured to be implanted within the patient's body to deliver the configured stimulation to another portion of one or more subdiaphragmatic branches of the patient's vagus nerve to decrease the patient's hunger and/or increase the patient's satiety.

2. The system of claim 1, wherein the processing device is located outside a body of the patient.

3. The system of claim 1, wherein the one or more recording electrodes and the one or more stimulation electrodes are configured to be at least partially implanted within a portion of the one or more subdiaphragmatic branches of the patient's vagus nerve.

4. The system of claim 1, wherein the one or more recording electrodes, the processing device, and the one or more stimulating electrodes are combined in a single, implantable device.

5. The system of claim 1, wherein the stimulation is configured to treat obesity.

6. The system of claim 1, wherein the stimulation is configured to treat a gastric disease and/or a metabolic disease.

7. The system of claim 1, wherein the processing device is a signal processing chip or a computing device.

8. The system of claim 1, wherein the processing device saves the decoded vagal activity signals for future analysis.

9. The system of claim 1, wherein at least one of the one or more recording electrodes and the one or more stimulating electrodes comprise carbon nanotube yarn.

10. The system of claim 9, wherein at least one of the one or more recording electrodes and the one or more stimulating electrodes is configured to be implanted intrafascicularly.

11. A method comprising:

during a training period:

receiving, by a system comprising a processor, one or more user inputs indicating times of hunger, amount and length of food intake, and/or satiety feelings after meals of a patient;

receiving, by the system, vagal activity signals recorded by one or more implanted recording electrodes in electrical communication with a portion of one or more subdiaphragmatic branches of a vagus nerve of the patient; and matching at least a portion of spike clusters of the vagal activity signals with each of the times of hunger, amount and length of food intake, and/or satiety feelings after meals; and after the training period:

receiving, by the system, the vagal activity signals recorded by the one or more implanted recording electrodes;

performing, by the system, signal processing to decode the vagal activity signals into a hunger, eating, and/or satiation event based on the matching during the training period;

configuring, by the system, a stimulation of an optimal type with an optimal timing based on the hunger, eating, and/or satiation event to decrease the patient's hunger and/or increase the patient's satiety; and sending, by the system, the stimulation to one or more implantable stimulating electrodes implanted within the patient's body to be applied to another portion of one or more subdiaphragmatic branches of the patient's vagus nerve.

12. The method of claim 11, wherein the stimulation is configured to treat at least one of obesity, irritable bowel disease, diabetes, and/or hypertension.

13. The method of claim 11, wherein the stimulation is configured to reduce vagal activity or increase vagal activity based on the decoded vagal activity signals.

14. The method of claim 13, wherein the stimulation is configured to reduce the vagal activity when the vagal activity signals related to hunger are received.

15. The method of claim 13, wherein the stimulation is configured to increase the vagal activity when the vagal activity signals related to satiety are received.

16. The method of claim 11, wherein the system is located outside the patient's body.

* * * * *